United States Patent [19]
Timpe et al.

[11] Patent Number: 6,063,404
[45] Date of Patent: May 16, 2000

[54] BIOADHESIVE TABLET

[75] Inventors: Carsten Timpe, Wessenborn; Michael Dittgen, Apolda; Detlef Grawe, Kleinromstedt; Jochen Schumacher, Jena; Holger Zimmermann, Ilmenau-Roda; Herbert Hoffmann, Jena, all of Germany

[73] Assignee: Jenapharm GmbH & Co. KG, Jena, Germany

[21] Appl. No.: 09/124,577

[22] Filed: Jul. 29, 1998

[30] Foreign Application Priority Data

Jul. 30, 1997 [DE] Germany .................. 197 34 538

[51] Int. Cl.$^7$ ................. A61K 9/20; A61K 9/44
[52] U.S. Cl. .......... 424/464; 424/435; 424/465; 424/467; 424/499; D24/101
[58] Field of Search .............. 424/435, 464, 424/465, 499, 467; D24/107

[56] References Cited

U.S. PATENT DOCUMENTS

| | | | |
|---|---|---|---|
| D. 375,157 | 10/1996 | Kramer et al. | D24/101 |
| D. 405,879 | 2/1999 | Leonard | D24/101 |
| 4,755,386 | 7/1988 | Hsiao et al. | 424/435 |
| 4,886,669 | 12/1989 | Ventouras | 424/469 |
| 4,915,948 | 4/1990 | Gallopo et al. | 424/435 |
| 5,007,790 | 4/1991 | Shell | 424/451 |
| 5,352,455 | 10/1994 | Robertson | 424/436 |

FOREIGN PATENT DOCUMENTS

| | | |
|---|---|---|
| 285551 | 12/1990 | Germany . |
| 9200765 | 5/1992 | Germany . |
| 4139883 | 6/1993 | Germany . |
| 2047093 | 11/1980 | United Kingdom . |
| 2252043 | 7/1992 | United Kingdom . |
| 8704342 | 7/1987 | WIPO . |

OTHER PUBLICATIONS

Duchene, D. et al., "Pharmaceutical and Medical Aspects of Bioadhesives Systems for Drug Administration", Drug Dev. Ind. Pharm., 14, (1988), pp. 283–318.

Peppas, N.A. et al., "Surface, Interfacial and Molecular Aspects of Polymer Bioadhesion on Soft Tissues", J. Controlled Release 2, (1985), pp. 257–275.

Park K. et al., "Bioadhesive Hydrogels", Chapter 8 Hydrogels Med. Pharm. vol. III (1987) pp. 151–175.

Ishida, M. et al., "New Mucosal Dosage Form of Insulin", Chem. Pharm. Bull., 29, (3), pp. 810–816.

Junginger, H.E. et al., "Bioadhasive Arzneistoffabgabesysteme und Arneiformen fur perorale und rektale Anwendung" Dtsch. Apoth. Ztg. 130, (1990) pp. 791–801.

Junginger, H.E. et al., "Moderne Arzneiformen zur lokalen und systemischen Wirkung im Mund–und Rachenraum" Dtsch. Apoth. Ztg. 131, (1991) pp. 1337–1348.

Veillard, M. Chapter IX, Buccal and Gastrointestinal Drug Delivery Systems, Bioadhesion—Possibilities and Future Trends, Wiss. Verlagsgesellschaft mbH Stuttgart (1990), pp. 124–139.

Robinson, J.R. et al., Ocular Drug Delivery Mechanism(s) of Corneal Drug Transport and Mucoadhesive Delivery Systems, S.T.P. Pharma 5 (12) (1989) pp. 839–846.

Saettone, M.F. et al., Evaluation of Muco–Adhesive Properties and In Vivo Activity of Ophthalmic Vehicles Based on Hyaluronic Acid, Int. J. Pharm. 51, pp. 203–212.

Satoh, K. et al., "Factors Effecting the Bioadhesive Property of Tablets Consisting of Hydroxypropyl Cellulose and Carboxyvinyl Polymer" Chem. Pharm. Bull. 37, (5) (1989) pp. 1366–1368 von Bruchhausen, F. et al., Hagers Handbuch der pharmazeutischen Praxis, "Methoden" 4th edition, 1967–1989, Springer Verlag, Berlin.

(List continued on next page.)

*Primary Examiner*—Thurman K. Page
*Assistant Examiner*—Lakshmi Channavajjala
*Attorney, Agent, or Firm*—Webb Ziesenheim Logsdon Orkin & Hanson, P.C.

[57] ABSTRACT

This invention relates to a bioadhesive tablet containing at least one bioadhesive adjuvant and at least one lubricant, with at least one surface of the tablet comprising concentric or parallel, straight and/or curved depressions, and to a method for producing the bioadhesive tablets as well as to pharmaceuticals in the form of the bioadhesive tablets.

15 Claims, 2 Drawing Sheets

OTHER PUBLICATIONS von Kerstin Herold, V., "Entwicklung, Untersuchung und Optimierung einer bukkalen, bioadhäsiven Progesteron–Zweischichttablette".

Dittrich, F., "Entwicklung einer neuen Bioadhäsiven Tablette zur enteralen und vaginalen Anwendung und Untersuchung einiger ihrer wesentlichen Eigenschaften in vitro und in vivo", Dissertation Univ. Greifswald (1982) pp. 64–65.

BIOADHESIVE TABLET

BACKGROUND OF THE INVENTION

1. Field of the Invention

This invention relates to a bioadhesive tablet containing at least one bioadhesive adjuvant and at least one lubricant, with at least one surface of said tablet comprising concentric or parallel, straight and/or curved depressions, and to a method for producing said bioadhesive tablets as well as to pharmaceuticals in the form of said bioadhesive tablets.

2. Prior Art

Bioadhesive pharmaceuticals that temporarily adhere to biological tissue while they release their active agent have been known for about 10 years. These bioadhesive or mucosa-adhesive pharmaceuticals are expected to solve bioavailability problems resulting from a too short retention time of the active agents at the place of resorption by adhering to mucosae. In particular, bioadhesive pharmaceuticals can bring about preferred resorption of the active agent at specified mucosae, e.g. of the gastro-intestinal tract.

Adhesion of this type of pharmaceuticals to the place of resorption is facilitated by bioadhesive polymers among which hydrogel-forming substances such as cellulose derivatives (hydroxyethyl cellulose (HEC), sodium carboxymethyl cellulose (NaCMC)), cross-linked polyacrylic acid (Carbopol®) and other carboxyvinyl polymers (Eudragit®), tragacanth gum and alginates are said to have the greatest efficacy. A survey (Duchene, D.; Touchard, F; Peppas, N. A.: Drug Dev. Ind. Pharm. 14, 283 (1988) ) described bioadhesive pharmaceuticals, e.g. tablets, films, plaster, gels and capsules that act locally or on the system and are primarily administered orally (buccally) but can also be applied perorally (gastro-intestinal tract), periocularly, nasally, vaginally, or rectally. Carboxyvinyl polymers (Carbopol® or Polycarbophil®) and cellulose derivatives (hydroxypropyl cellulose (HPC), HEC or NaCMC) or mixtures of both component were mentioned as bioadhesive polymers for these pharmaceuticals. In particular, carboxyvinyl polymers and compounds derived from them are suited as bioadhesive polymers (Peppas, N. A.; Buri, P. A.; J. Controlled Release 2, p. 257 (1985); Park, K.; Cooper, S. L.; Robinson, J. R.: Hydrogels Med. Pharm. 3, p. 151 (1987)).

DD 285 551 A5 relates to a method for the production of bioadhesive pharmaceuticals, for example, tablets, granulates or mucilages containing a copolymerisate that is capable of swelling in water and comprises a maximum of 25 percent by mass of monomers with carboxyl functions, mainly characterized by a content of foreign matter of up to 0.56 percent by mass, and further characterized in that it is produced using a maximum of 0.5 percent by mass of an anionic emulgator and a maximum of 0.06 percent by mass of an initiator.

The solid bioadhesive pharmaceuticals known so far are decomposed slowly, as a rule. Frequently the unchanged form of the pharmaceutical, for example, microparticles but most frequently two- or multilayer tablets, is brought into contact with the tissue. Only a more or less narrowly limited area is therefore available for resorbing the active agent. This area can be further reduced by the beginning swelling of the respective form of application depending on the bioadhesive polymer used. This is the case, for example, for a coated bioadhesive tablet that is capable of swelling and consists of a core containing the active agent and a bioadhesive coating (Ishida, M.; Machida, Y.; Nambu, N.; Nagai, T.: Chem. Pharm. Bull. 29, p. 810 (1981)).

Bioadhesive microspheres presented recently also contain the active agent in their core and are coated with a layer of a bioadhesive polymer (Junginger, H. E.; Lehr, C. M.: Dtsch. Apoth. Ztg. 130, p. 791 (1990)). A diffusion layer can be formed during the swelling process that adversely affects the passage of the pharmaceutical.

Thus bioadhesive tablets such as buccal tablets are mostly described as two- or multilayer tablets that release the active agent in a controlled way (Junginger, H. E.; de Vries, M. E.; Bodde, H. E.: Dtsch. Apoth. Ztg. 131, p. 1337 (1991)). These tablets adhere to the tissue at first due to capillary effects, and later, following hydration and swelling, due to bonds resulting from the interdiffusing bioadhesive polymer.

Other bioadhesive tablets, especially buccal tablets (Veillard, M. in: Gurny, R.; Junginger, H. E. (eds.) "Bioadhesion—Possibilities and Future Trends", p. 124, APV-Paperback, Wiss. Verlagsgesellschaft, Stuttgart 1990), only show limited swelling and are therefore particularly suited for long-term adhesion to the tissue. As an exception, bioadhesive mucilages, i.e. aqueous preparations (Robinson, J. R.: S.T.P. Pharma 5, p. 839 (1989)) or a tablet that swells to form a mucilage (DE 4 139 883 A1) are used. These show lower adhesion to the tissue than the solid forms or their decomposition products (Saettone, M. F.; Chetoni, P.; Torracca, M. T.; Burgalassi, S.; Giannaccini, B.: Int. J. Pharm. 51, p. 203 (1989)), and they have the known disadvantages of being susceptible to microorganisms and containing unstable active agents.

Furthermore, a number of fast decaying pharmaceuticals can be found that do not come close to the pharmaceuticals of the invention because of their rapid decomposition. For example, U.S. Pat. No. 5,007,790 relates to tablets and capsules containing polymers capable of swelling for application in the gastro-intestinal tract.

U.S. Pat. No. 4,886,669 describes tablets comprising microparticles that contain the active agent, a decomposition adjuvant, and a swelling agent. The product of rapid decomposition of the tablets in water is a high-viscosity suspension. It is known, however, that there is no direct connection between viscosity and bioadhesion (Dittgen, M.; Oestereich, S.; Dittrich, F.: Pharmazie 44, p. 460 (1989), Satoh, K.; Takayama, K.; Machida, Y.; Suzuki, Y.; Nakagaki, M.; Nagai, T.: Chem. Pharm. Bull. 37, p. 1366 (1989)).

It is the problem of the present invention to overcome the disadvantages of the bioadhesive tablets known so far. In particular, it is a problem of the invention to improve the passage of the active agents contained therein through the mucosa.

SUMMARY OF THE INVENTION

This problem is solved according to the invention by a bioadhesive tablet containing at least one bioadhesive adjuvant and at least one lubricant, with at least one surface of said tablet comprising concentric or parallel, straight and/or curved depressions.

The bioadhesive tablets of the invention are decomposed in such a way that they or their decomposition products do not impair by swelling the passage of the active agents they contain through the mucosa. The tablets of the invention are a solid substance but nevertheless constitute a bioadhesive form of pharmaceutical in the organism that protects its active agents against microbial attacks, and from which said active agents are made available for resorption across an extensive tissue area of the target organ.

The bioadhesive tablets of the invention nearly completely release the active agent they contain and stimulate its resorption by the tissue while not entering into any undesirable interaction with the biological tissue.

The bioadhesive adjuvant should preferably be a substance that develops adhesion when coming into contact with the mucosa, such as a cellulose, a cellulose derivative, a carboxyvinyl polymer, a derivative of a carboxyvinyl polymer, a lectin or natural material or mixtures of said substances.

It is furthermore considered advantageous that the lubricant facilitates tabletting of cohesive mixtures as do talc, a metallic soap, a fatty acid, or mixtures of said substances.

Furthermore, it is advantageous according to the invention that the content of bioadhesive adjuvant of a tablet is between 5 and 65 percent by weight, preferably between 10 and 45 percent by weight, and the lubricant content between 0.05 and 5 percent by weight, preferably between 1 and 3 percent by weight, and that the lubricant/bioadhesive adjuvant ratio is between 1:1300 and 1:1, preferably between 1:10 and 1:15.

It is particularly advantageous that the tablet surface comprises 2 to 12, preferably 3 to 5, concentric or parallel straight and/or curved depressions with a depth between 0.1 mm and 1.0 mm, preferably between 0.3 mm and 0.6 mm, measured from the surface of the tablet, said depressions being at a spacing between 0.5 and 5 mm, preferably between 1.5 and 2.5 mm, and shaped like notches, the flanks of said notches having a circular convexity the radius of which is in the range from 0.1 to 0.9 mm, preferably 0.5 mm, and/or the aperture angle of said notches being between 45 and 135°, preferably 90°.

Another object of the present invention is a method for producing bioadhesive tablets which includes intermixing at least one bioadhesive adjuvant with at least one lubricant and pressing a tablet having at least one surface with concentric or parallel straight and/or curved depressions.

A preferred method according to the invention for producing bioadhesive tablets is characterized in that the bioadhesive adjuvant is a substance that develops adhesion when it comes into contact with the mucosa, such as a cellulose, a cellulose derivative, a carboxyvinyl polymer, a derivative of a carboxyvinyl polymer, a lectin or natural material or mixtures of said substances.

Another preferred method for producing bioadhesive tablets is characterized in that the lubricant facilitates tabletting of cohesive mixtures as do talc, a metallic soap, a fatty acid, or mixtures of said substances.

Particularly preferred is a method according to the invention for producing bioadhesive tablets wherein the content of bioadhesive adjuvant of a tablet is between 5 and 65 percent by weight, preferably between 10 and 45 percent by weight, and the lubricant content between 0.05 and 5 percent by weight, preferably between 1 and 3 percent by weight, and wherein the lubricant/bioadhesive adjuvant ratio is between 1:1300 and 1:1, preferably between 1:10 and 1:15.

Particularly preferred is a method for producing bioadhesive tablets in which the tablet surface comprises 2 to 12, preferably 3 to 5, concentric or parallel straight and/or curved depressions with a depth between 0.1 mm and 1.0 mm, preferably between 0.3 mm and 0.6 mm, measured from the surface of the tablet, said depressions being at a spacing between 0.5 and 5 mm, preferably between 1.5 and 2.5 mm, and shaped like notches, the flanks of said notches having a circular convexity the radius of which is in the range from 0.1 to 0.9 mm, preferably 0.5 mm, and/or the aperture angle of said notches being between 45 and 135°, preferably 90°.

Another object of the present invention are pharmaceuticals that are present in the form of the bioadhesive tablets according to the invention and that contain active agents of the most varied fields of indication.

An object of the present invention are, in particular, pharmaceuticals in the form of the bioadhesive tablets according to the invention containing as active agents antirheumatics, analgesics, antiparkinson agents, β-adrenergic receptor blockers, sexual hormones, contraceptives, cardiovascular agents, sleeping and hypophyseal hormones, antidiabetics, immunotherapeutic agents, or anticoagulants.

The bioadhesive tablets of the invention can be produced in a known way. Any active agent, especially medicinal substances, can be moulded into tablets that adhere to the mucosa by adding a bioadhesive adjuvant, a lubricant, and optionally other adjuvants common in tabletting using a simple technique. In the organism, the bioadhesive tablet is to adhere to the mucosa immediately upon contacting it, to develop as large a contact area as possible with the mucosa, while containing exclusively toxicologically safe adjuvants that favour resorption of the active agents.

The medicinal substances that can be used are all those for which a guaranteed or controlled bioavailability can be useful. No specification is made as to their intensity or sphere of action so that, for example, antirheumatics, analgesics, antiparkinson agents, β-adrenergic receptor blockers, sexual hormones, especially contraceptives, cardiovascular agents, sleeping and hypophyseal hormones, antidiabetics, immunotherapeutic agents, anticoagulants and other medicinal substances can be included in bioadhesive tablets produced in accordance with the method of the invention. In addition, no specification is made as to the place of resorption of this form of pharmaceutical. The invention is preferably suited for producing bioadhesive pharmaceuticals administered perorally and vaginally.

An object of the present invention are therefore pharmaceuticals for oral, peroral, rectal, or vaginal application containing a pharmaceutically active agent besides the common substrates and diluents.

The pharmaceuticals according to the invention are produced in a generally known way at an appropriate dosage depending on the intended application using the common solid or liquid substrates or diluents and adjuvants commonly used in pharmaceutical engineering. Preferred preparations are those forms suitable for oral, rectal, or vaginal administration. Suitable techniques are described, for example, in "Hagers Handbuch der pharmazeutischen Praxis, 4th edition, 1967–89, Springer Verlag, Berlin".

The respective tablets can be produced, for example, by intermixing the active substance with known adjuvants, for example, inert diluents such as dextrose, sugar, sorbitol, mannitol, polyvinylpyrrolidone, blasting agents such as maize starch or alginic acid, binders such as starch or gelatin, lubricants such as magnesium stearate or talcum and/or materials by which to produce a depot effect such as carboxyl polymethylene, carboxymethyl cellulose, cellulose acetate phthalate or polyvinyl acetate. The tablets may consist of several layers.

BRIEF DESCRIPTION OF THE DRAWINGS

The invention will be explained in greater detail below with reference to the examples of execution and the associated figures, where.

DETAILED DESCRIPTION OF THE PREFERRED EMBODIMENTS

Figure 1:
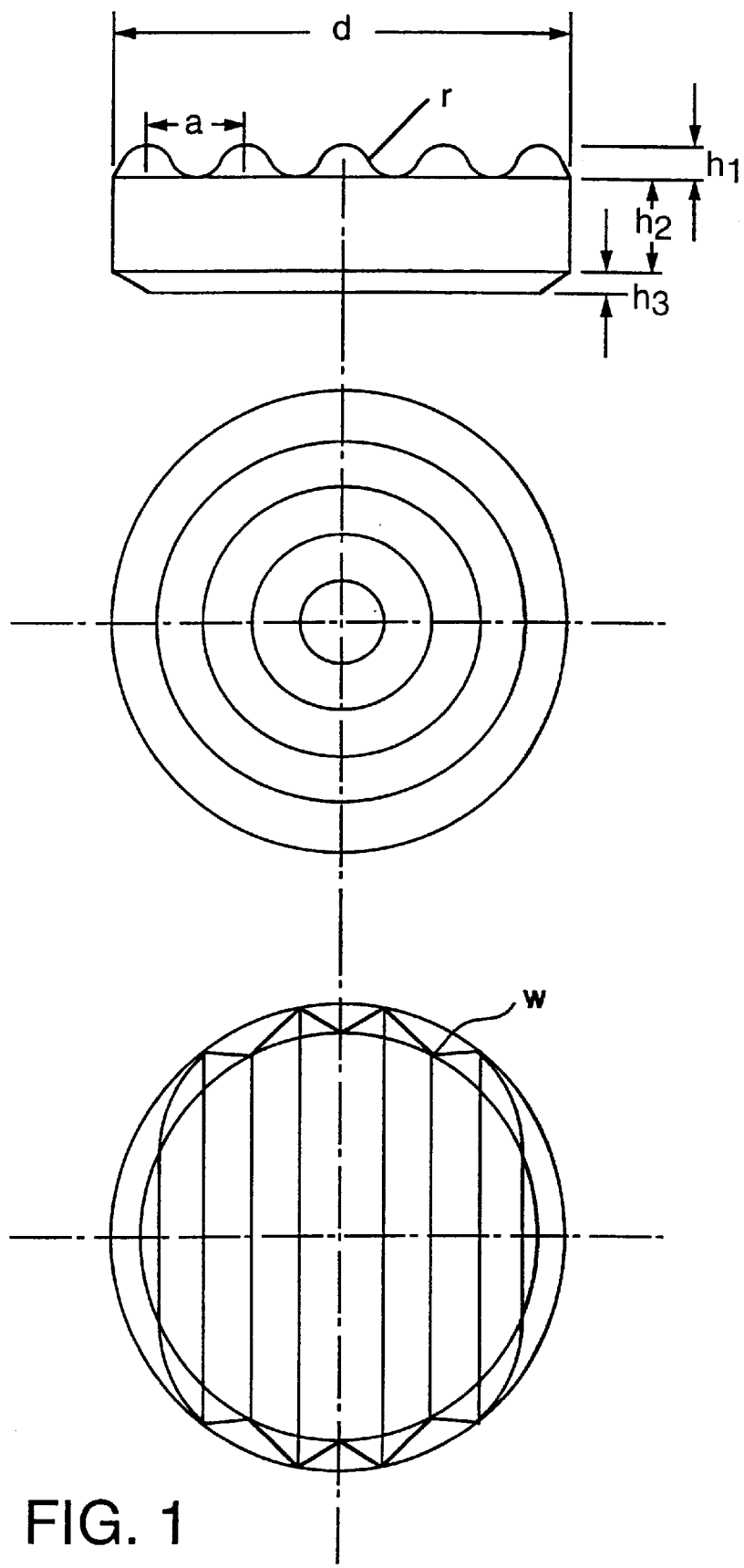
FIG. 1 shows a cross-section of a bioadhesive tablet, a top view with concentric depressions, and a top view with parallel straight and/or curved depressions.

FIG. 1 represents the solution according to the invention of the problem of the invention with reference to an embodiment of the bioadhesive tablet according to the invention. This tablet is characterized in that a rough surface is formed by producing depressions on at least one side of it in the pressing process. It was found, surprisingly, that a suitable rough surface is provided in particular by round and/or angular, especially rectangular depressions, the number and spacing of which is in balanced proportion with the surface area. In particular, the following dimensions of the depressions and other tablet parameters have proved to be useful:

a spacing between two depressions, 0.5 to 5 mm, preferably 1.5 to 2.5 mm, d tablet diameter, 3 to 15 mm, preferably 7 to 9 mm, $h_1$ depth of the depressions, 0.1 mm to 1.0 mm, preferably 0.3 mm to 0.6 mm, $h_2$ root face width of the tablets, 0.1 to 8 mm, preferably 0.2 to 0.4 mm $h_3$ bevel height, 0.05 mm to 2.0 mm, preferably 0.1 mm to 1.0 mm, r depression radius, 0.1 to 0.9 mm, preferably 0.5 mm w angle of depression, 45 to 135°, preferably 90°.

Figure 2:
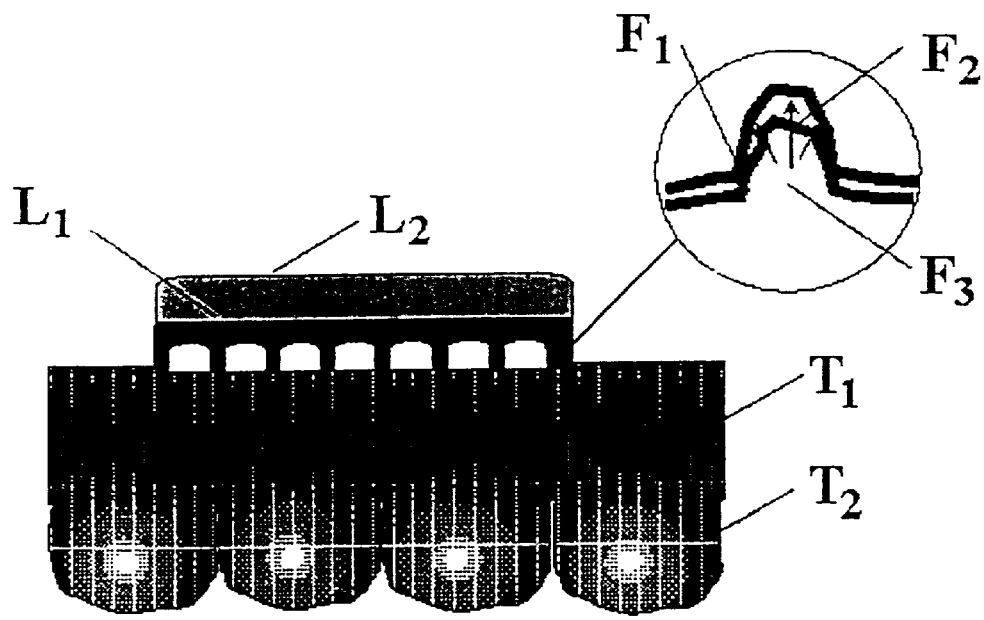
FIGS. 2a and 2b show a bioadhesive tablet at its place of resorption

FIGS. 2a and 2b show the mode of action of the tablets according to the invention at the place of action or resorption. The tablet adheres to the mucosa immediately upon contacting it due to its surface shaped according to the invention. As a result of its tuned geometry, the acting forces are adhesive ($F_1$), swelling ($F_2$), and interfacial tension ($F_3$) forces. The medicinal substance, unless completely or partly contained in the bioadhesive layer ($L_1$), can easily pass through said layer in those parts of the depressions that are not in contact with the mucosa, thus guaranteeing high bioavailability.

Figure 3:
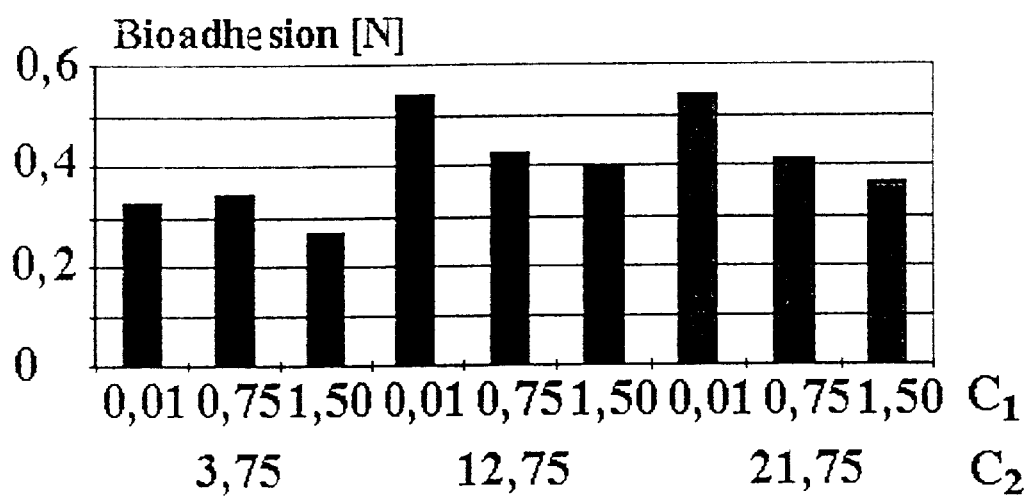
FIG. 3 shows the bioadhesion of various bioadhesive tablets containing differing quantities of a lubricant ($C_1$, mg) and a bioadhesive adjuvant ($C_2$, mg).

FIG. 3 shows the dependency of bioadhesion as measured on a dialysis membrane (Visking 36/32 of Roth GmbH & Co. D-Karlsruhe, method: Herold, K., Entwicklung, Untersuchung und Optimierung einer bukkalen, bioadhäsiven Progesteron-Zweischichttablette, Diplomarbeit, Univ. Halle (Pharmazie) 1997) on the lubricant/bioadhesive adjuvant ratio. A tablet according of the invention invariably contains a bioadhesive adjuvant and a lubricant that facilitates tabletting. These two auxiliary agents are antagonists. The bioadhesive adjuvant easily sticks and adheres. The lubricant prevents sticking and adherence. In addition, the desired adhesion effects of the required quantity of bioadhesive adjuvants added are weakened by the lubricant added. It was found, surprisingly, that for a specific and relatively limited lubricant/bioadhesive adjuvant ratio in the range from 1:1300 to 1:1, preferably in the range from 1:10 to 1:15, both tabletting and the desired bioadhesive effect at the mucosa can be achieved.

The examples below shall explain the invention without limiting or restricting it in any way.

Example 1

| Bioadhesive tablet containing progesterone (oral application) | |
|---|---|
| Progesterone | 20.0 g |
| Cyclodextrin | 100.0 g |
| Mannitol | 100.0 g |
| Vehicle | 5.5 g |

The ingredients are mixed and moulded into tablets in the known way. Bioadhesion of the tablets as tensiometrically determined ex vivo on a fresh pig's small bowel after a contact time of 5 minutes (Dittrich, F., Entwicklung einer neuen bioadhesive tablette zur enteralen und vaginalen Anwendung und Untersuchung einiger ihrer wesentlichen Eigenschaften in vitro und in vivo, Dissertation Univ. Greifswald 1982, pp. 64–65) is 0.62 N.

Example 2

| Bioadhesive tablet containing estradiol (vaginal application) | |
|---|---|
| Estradiol, co-micronized | 50 mg |
| Fructose | 48 mg |
| Lactose-Monohydrate | 15 mg |
| Sodium carboxymethyl cellulose | 15 mg |
| Glycerol palmitostearate | 2 mg |

The ingredients are mixed and moulded into tablets in the known way. Bioadhesion of the tablets as tensiometrically determined ex vivo on a fresh pig's small bowel after a contact time of 5 minutes(see Example 1) is 0.58 N.

Example 3

| Bioadhesive two-layer tablet containing testosterone (oral application) | |
|---|---|
| Active agent layer: | |
| Testosterone comicronisate | 50 mg |
| Mannitol | 48 mg |
| Cellactose | 30 mg |
| Hydroxyethyl cellulose | 1 mg |
| Talc | 4 mg |
| Magnesium stearate | 1 mg |
| Bioadhesive layer: | |
| Mannitol | 18 mg |
| Cellactose | 35 mg |
| Sodium carboxymethyl cellulose | 10 mg |
| Talc | 1 mg |
| Magnesium stearate | 1 mg |
| Iron oxide LMF red 30 | 0.05 mg |

The ingredients are mixed and moulded into tablets in the known way. Bioadhesion of the tablets as tensiometrically determined ex vivo on a fresh pig's small bowel after a contact time of 5 minutes(see Example 1) is 0.88 N.

Example 4

| Bioadhesive two-layer tablet containing dehydroepiandrosterone (rectal application) | |
|---|---|
| Active agent layer: | |
| Dehydroepiandrosterone comicronisate | 50 mg |
| Laevulose | 52 mg |
| Cellactose | 30 mg |
| Hydroxyethyl cellulose | 5 mg |
| Talc | 4 mg |
| Magnesium stearate | 1 mg |
| Bioadhesive layer: | |
| Laevulose | 8 mg |
| Cellactose | 45 mg |
| Sodium carboxymethyl cellulose | 15 mg |
| Talc | 1 mg |
| Magnesium stearate | 1 mg |
| Iron oxide LMF red 30 | 0.05 mg |

The ingredients are mixed and moulded into tablets in the known way. Bioadhesion of the tablets as tensiometrically determined ex vivo on a fresh pig's small bowel after a contact time of 5 minutes(see Example 1) is 0.36 N.

List of Reference Symbols a spacing between two depressions
d tablet diameter
$h_1$ depth of depressions
$h_2$ root face width of the tablets
$h_3$ bevel height
r depression radius
w angle of depression
$F_1$ adhesion
$F_2$ swelling
$F_3$ interfacial tension
$L_1$ bioadhesive layer
$L_2$ active agent layer
$T_1$ mutilage layer
$T_2$ epithelium

We claim:

1. A bioadhesive tablet containing at least one bioadhesive adjuvant, at least one pharmaceutically active agent and at least one lubricant, with at least one surface of said tablet comprising concentric or parallel, straight or curved depressions or both, said depressions being shaped like notches, the aperture angle of said depressions being between about 45° and about 135°, the flanks of said depressions having a circular convexity which is in the range from about 0.1 to about 0.9 mm, and said depressions having a depth which is in the range from about 0.1 mm to about 1.0 mm.

2. The bioadhesive tablet according to claim 1 wherein the bioadhesive adjuvant is a substance that develops adhesion when it comes into contact with the mucosa.

3. The bioadhesive tablet according to claim 2 wherein the bioadhesive adjuvant is selected from the group consisting of cellulose, a cellulose derivative, a carboxyvinyl polymer, a derivative of a carboxyvinyl polymer, a lectin or natural material and mixtures thereof.

4. The bioadhesive tablet according to claim 1 wherein the lubricant facilitates tableting of cohesive mixtures.

5. The bioadhesive tablet according to claim 4 wherein the lubricant is selected from the group consisting of talc, a metallic soap, a fatty acid and mixtures thereof.

6. The bioadhesive tablet according to claim 1 wherein the content of bioadhesive adjuvant of said tablet is between 5 and 65 percent by weight and the lubricant content is between 0.05 and 5 percent by weight and wherein the lubricant/bioadhesive adjuvant ratio is between 1:1300 and 1:1.

7. The bioadhesive tablet according to claim 1 wherein the tablet surface comprises 2 to 12 concentric or parallel, straight or curved depressions or both with a depth between 0.1 mm and 1.0 mm measured from the surface of the tablet, said depressions being at a spacing between 0.5 and 5 mm and shaped like notches, the flanks of said notches having a circular convexity the radius of which is in the range from 0.1 to 0.9 mm or the aperture angle of said notches being between 45 and 135° or both.

8. A method for producing bioadhesive tablets comprising the steps of;

intermixing at least one bioadhesive adjuvant with at least one lubricant and at least one pharmaceutically active agent; and pressing a tablet at least one surface of which comprises concentric or parallel, straight or curved depressions or both, said depressions being shaped like notches, the aperture angle of said depressions being between about 45° and about 135°, the flanks of said depressions having a circular convexity which is in the range from about 0.1 to about 0.9 mm, and said depressions having a depth which is in the range from about 0.1 mm to about 1.0 mm.

9. The method for producing bioadhesive tablets according to claim 8 wherein the bioadhesive adjuvant is a substance that develops adhesion when it comes into contact with the mucosa.

10. The method for producing bioadhesive tablets according to claim 9 wherein the bioadhesive adjuvant is selected from the group consisting of cellulose, a cellulose derivative, a carboxyvinyl polymer, a derivative of a carboxyvinyl polymer, a lectin or natural material and mixtures thereof.

11. The method for producing bioadhesive tablets according to claim 8 wherein the lubricant facilitates tableting of cohesive mixtures.

12. The method for producing bioadhesive tablets according to claim 11 wherein the lubricant is selected from the group consisting of talc, a metallic soap, a fatty acid and mixtures thereof.

13. The method for producing bioadhesive tablets according to claim 8 wherein the content of bioadhesive adjuvant of said tablet is between 5 and 65 percent by weight and the lubricant content between 0.05 and 5 percent by weight and wherein the lubricant/bioadhesive adjuvant ratio is between 1:1300 and 1:1.

14. The method for producing bioadhesive tablets according to claim 8 wherein the tablet surface comprises 2 to 12 concentric or parallel, straight or curved depressions or both with a depth between 0.1 mm and 1.0 mm measured from the surface of the tablet, said depressions being at a spacing between 0.5 and 5 mm and shaped like notches, the flanks of said notches having a circular convexity the radius of which is in the range from 0.1 to 0.9 mm or the aperture angle of said notches being between 45 and 135° or both.

15. A pharmaceutical in the form of a bioadhesive tablet made according to claim 1, containing as active agent antirheumatics, analgesics, antiparkinson agents, β-adrenergic receptor blockers, sexual hormones, contraceptives, cardiovascular agents, sleeping and hypophyseal hormones, antidiabetics, immunotherapeutic agents, or anticoagulants.

* * * * *

UNITED STATES PATENT AND TRADEMARK OFFICE
CERTIFICATE OF CORRECTION

PATENT NO.   : 6,063,404
DATED        : May 16, 2000
INVENTOR(S)  : Carsten Timpe et al.

It is certified that error appears in the above-identified patent and that said Letters Patent is hereby corrected as shown below:

In the Drawings:
Substitute attached sheet 2 of 2 for pinted sheet 2 of 2 of the drawings.

Title Page,
Under [56] References Cited,

Column 2,
Line 27, between "1366-1368" and "von Bruchhausen" insert a new paragraph.

Column 8, Claim 8:
Line 15, "of;" should read -- of: --.

Signed and Sealed this

Twenty-eighth Day of August, 2001

*Attest:*

*Attesting Officer*

NICHOLAS P. GODICI
*Acting Director of the United States Patent and Trademark Office*

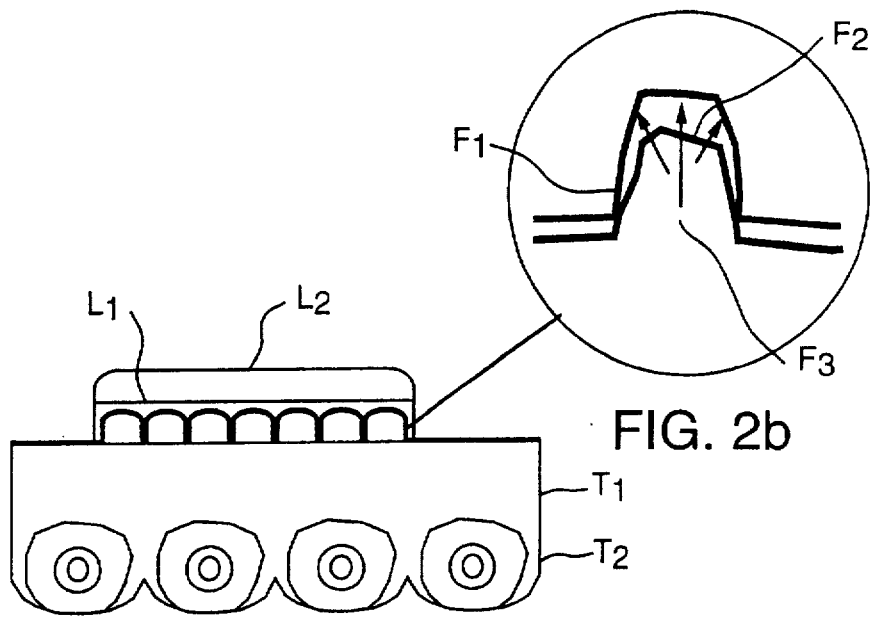
FIG. 2b
FIG. 2a
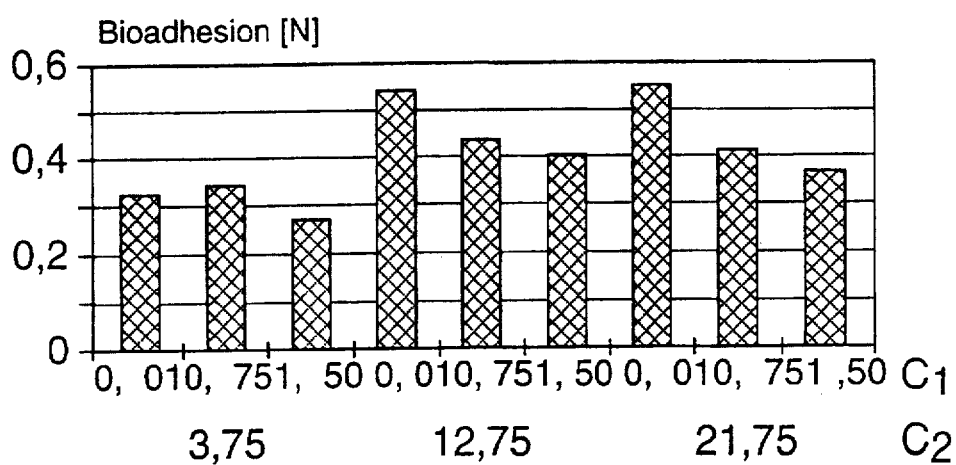
FIG. 3